United States Patent [19]

Rogers et al.

[11] 4,359,397
[45] Nov. 16, 1982

[54] BENZOTRIAZOLE COMPLEXES AND FILM UNITS EMPLOYING SAME

[75] Inventors: Howard G. Rogers, Weston; Robert D. Eckert; Ronald A. Sahatjian, both of Lexington; Robert A. Sulesky, Georgetown, all of Mass.

[73] Assignee: Polaroid Corporation, Cambridge, Mass.

[21] Appl. No.: 221,845

[22] Filed: Dec. 31, 1980

[51] Int. Cl.³ .................................................. C09K 3/00
[52] U.S. Cl. ..................................... 252/194; 430/449; 430/354
[58] Field of Search ............. 548/257; 252/49.3, 49.7, 252/51.5 R, 156, 194; 430/449

[56] References Cited

U.S. PATENT DOCUMENTS

| T 878,008 | 9/1970 | Padday . | |
|---|---|---|---|
| 2,704,721 | 3/1955 | Land | 430/248 |
| 3,080,230 | 3/1963 | Haydn et al. | 430/254 |
| 3,248,219 | 4/1966 | Jacobs | 430/566 |
| 3,564,001 | 2/1971 | Long | 548/257 |
| 3,694,204 | 9/1972 | Farney et al. | 430/203 |
| 3,733,199 | 5/1973 | Crough et al. | 430/456 |
| 3,806,342 | 4/1974 | Farney et al. | 430/203 |
| 4,107,060 | 8/1978 | Schick et al. | 548/257 |

FOREIGN PATENT DOCUMENTS 1175075 2/1965 Fed. Rep. of Germany .
1948794 4/1971 Fed. Rep. of Germany .

Primary Examiner—J. Travis Brown
Attorney, Agent, or Firm—Louis G. Xiarhos

[57] ABSTRACT

Solid compositions are disclosed comprising a complex of water; a benzotriazole of the formula

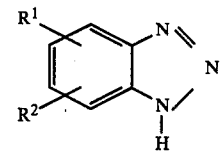

wherein $R^1$ and $R^2$ are independently hydrogen, a monovalent organic radical, halogen, or nitro; and at least one water-soluble base having a basicity greater than that of the benzotriazole and capable of dissociating to provide an anion and a monovalent or divalent metal cation. The compositions have melting ranges above 35° C. and are capable of releasing a substantial portion of the water contained therein to the surrounding environment when melted. The compositions can be employed in thermally developable photographic film units as thermally induced water-releasing materials which provide water to the internal environment of the film unit when the film unit is heated sufficiently to melt the composition.

32 Claims, 3 Drawing Figures

BENZOTRIAZOLE COMPLEXES AND FILM UNITS EMPLOYING SAME

BACKGROUND OF THE INVENTION

This invention relates to chemical compositions and, in particular, to chemical compositions which can be used as sources of water in thermally developable photographic film units.

Thermally developable photographic film units are known. In such film units, image formation is effected by simply heating the film unit subsequent to exposure. External processing compositions or baths are normally not employed during processing inasmuch as the reagents necessary to effect image formation are initially contained within the film unit structure and the application of heat is alone sufficient to initiate image formation.

Thermally developable film units heretofore known include those which comprise at least one silver halide emulsion layer and, in one or more layers, a thermally induced water-releasing material, i.e., a material capable of supplying water to the internal environment of the film unit when the film unit is heated. Generally, the water provided by such water-releasing materials is employed to activate one or more silver halide developing agents initially present in the film unit, thereby promoting development of the silver halide. Image formation is effected as a function of development. For example, silver halide reduced to silver in areas of development may be used as the image-forming material, or unreduced silver halide in areas where development has not occurred may be transferred to a receiving layer and reduced therein to provide the desired image.

In addition to activating a silver halide developing agent, the water provided by the water-releasing material may perform other functions depending on the image formation process intended to be operational in the film unit. For example, the water may function to activate a stabilizing agent as disclosed, for example, in U.S. Pat. No. 3,248,219; to promote colloid transfer of silver halide as disclosed, for example, in U.S. Pat. No. 3,080,320; or to facilitate diffusion transfer of soluble silver halide as disclosed, for example, in U.S. Pat. Office Defensive Publication No. T878,008, published Sept. 8, 1970.

Materials which have been disclosed to be useful as thermally induced water-releasing materials in thermally developable film units include water-in-wax emulsions as disclosed in the previously referenced U.S. Patent Office Defensive Publication No. T878,008; hydrated salts such as sodium citrate pentahydrate, sodium acetate trihydrate, calcium acetate dihydrate, trisodium phosphate dodecahydrate, and hydrated sodium sulfate as disclosed, for example, in previously referenced U.S. Pat. No. 3,080,230; substances which ensure a high residual moisture content such as glycol, glycerol, and sorbitol as disclosed, for example, in U.S. Pat. No. 3,080,230; alkali metal salts of polystyrol sulfonic acid, as disclosed in German Patent No. 1,175,075; and water-releasing agents such as Glauber salt (sodium sulfate decahydrate), borax, sodium triphosphate, sodium metasilicate, sodium alginate, and sugars as disclosed, for example, in previously referenced U.S. Pat. No. 3,248,219.

SUMMARY OF THE INVENTION

The present invention relates to novel compositions which can be used as thermally induced water-releasing materials in thermally developable film units. The instant compositions are capable of providing to the internal environment of a film unit a relatively large amount of water per weight of composition. In addition, the compositions of this invention allow flexibility in the choice of an operative processing temperature in that they may be formulated so as to release water in a variety of predetermined temperature ranges and, in particular, in a predetermined and relatively low range of temperatures, such that the quality of the resultant photographic image can be controlled. Other advantages obtained by utilization of the compositions hereof as water-releasing materials are described hereinafter.

Accordingly, it is an object of the present invention to provide compositions which can be employed as thermally induced water-releasing materials in thermally developable film units.

It is another object of the present invention to provide a method of preparation of the compositions of this invention.

It is another object of the present invention to provide thermally developable film units employing the compositions of this invention as water-releasing materials.

Other objects of this invention will become apparent from the description appearing hereinafter.

According to the present invention, certain compositions comprising complexes of a benzotriazole, water, and certain bases have been discovered which have melting ranges above about 35° C. and which possess a high content of water which can be released and rendered available to perform useful functions by simply melting the complex. The water of which the complexes of this invention are comprised is apparently loosely bound within the complex such that it is readily released in substantial quantity to the surrounding environment when the complex is melted.

More specifically, the compositions of this invention comprise complexes of water; a benzotriazole of the formula wherein $R^1$ and $R^2$ are independently hydrogen, a monovalent organic radical, halogen, or nitro; and at least one water-soluble base having a basicity greater than that of the benzotriazole and capable of dissociating to provide an anion and a monovalent or divalent metal cation. The complexes of which the compositions are comprised are solids at temperatures below about 35° C. and may be solids at temperatures above 35° C. depending on the particular complex and the melting range of the complex.

The complexes of this invention can be prepared by a process comprising the steps of mixing water, the above-described benzotriazole, and the above-described base under conditions of time and temperature such that a single phase liquid is obtained; and cooling the single phase liquid to a temperature at which it is converted to a solid; the benzotriazole, base, and water being mixed in proportions such that the solid obtained has a melting range above about 35° C.

It has been found that the complexes of this invention can be employed in thermally developable film units as thermally induced water-releasing materials. Accordingly, in another aspect of this invention, there are provided thermally developable film units comprising the complexes of this invention. More particularly, the present invention provides thermally developable film units comprising a support carrying on one surface a photosensitive silver halide emulsion layer, a silver halide developing agent, a layer comprising a complex of this invention, and a substantially water-impermeable barrier layer positioned within the film unit so as to retain the water released from the complex during thermal processing sufficiently within the film unit as to permit thermal processing thereof. Image formation is effected in such film units by imagewise exposing the silver halide emulsion; heating the film unit to a temperature sufficient to melt the complex; and maintaining the film unit at a processing temperature for a period of time effective to provide a visible image to the film unit.

For a fuller understanding of the nature and objects of this invention, reference should be had to the following detailed description taken in connection with the accompanying drawings.

DETAILED DESCRIPTION OF THE INVENTION

In accordance with the present invention, certain complexes of a benzotriazole, a base, and water have been discovered. These complexes have melting ranges above about 35° C. Accordingly, the complexes are solids at temperatures of below about 35° C. They may, however, be solids at temperatures above 35° C. depending on the particular complex and the melting range of the complex. It has been found that a substantial portion of the water contained in these complexes is released when the complex is melted, i.e., melting the complexes of this invention renders a substantial portion of the water contained therein available to perform useful functions in the surrounding environment of the complex.

As used herein, the term "solid" is used in its ordinary sense and means a substance which has a definite volume and shape and which resists forces which tend to alter its volume and shape. The term includes substances which are wax-like in physical character. The solid character of the complexes of this invention is important in that effective utilization of the complexes as water-releasing materials in thermally developable film units requires that they be capable of incorporation into such film units as discrete layers and, further, that they release water in quantity only when the film unit is heated. The complexes of this invention have proven suitable as water-releasing materials in that, as solids, they are capable of employment as discrete layers and contain the water as an entrapped or bound component which is not available to the internal environment of the film unit in substantial quantity until the film unit is heated to effect melting of the water-releasing complex.

The complexes of this invention are complexes of water, a benzotriazole of the formula wherein $R^1$ and $R^2$ are independently hydrogen, a monovalent organic radical, halogen, e.g., chloro or bromo, or nitro, and at least one water-soluble base having a basicity greater than that of the benzotriazole and capable of dissociating to provide an anion and a monovalent or divalent metal cation, e.g., $Na^+$, $K^+$, or $Ca^{++}$.

The term "benzotriazole" is used herein in a generic sense to refer to benzotriazole compounds as a class and as generally described hereinbefore and in a specific sense to refer to the compound, benzotriazole, per se. The benzotriazole may be substituted in the fashion described hereinbefore, with suitable substituents and substituion patterns being those which permit formation of the complexes of this invention. Preferably, if either of $R^1$ or $R^2$ is other than hydrogen, the substituents are in the 5- and 6-positions such that the benzotriazole is of the formula Monovalent organic radicals which may be employed as substituents $R^1$ or $R^2$ include lower alkyl, e.g., methyl, ethyl, propyl; aryl, e.g., phenyl; alkaryl, e.g., tolyl; aralkyl, e.g., benzyl; acyl, e.g., acetyl; and lower alkoxy, e.g., methoxy, ethoxy. Preferred substituents are hydrogen and lower alkyl, particularly methyl.

The complexes of this invention may be prepared by a process comprising the steps of mixing water, a benzotriazole of the formula wherein $R^1$ and $R^2$ are as previously defined, and at least one water-soluble base having the aforementioned characteristics, the mixing being conducted under conditions of time and temperature such that a single phase liquid is obtained; and cooling the single phase liquid to a temperature at which it is converted to a solid; the benzotriazole, base, and water being mixed in proportions such that the solid obtained has a melting range above about 35° C.

In accordance with the above process, the benzotriazole, base, and water can be mixed at a relatively low temperature, e.g., ambient room temperature of about 25° C., and heated sufficiently to effect formation of the single phase liquid. The named components can also be mixed initially at a temperature of about 40° C. to 100° C. and, most preferably, about 55° C. to 90° C. By mixing at these relatively higher temperatures, the single phase liquid is generally obtained in a minimal amount of time. Thus, the water and base can be mixed and heated to an appropriate temperature between 40° C. and 100° C. and the benzotriazole then added. A single phase liquid may be obtained almost instantaneously with such a procedure such that the mixture may be cooled immediately upon completion of the benzotriazole addition to prepare the desired solid complex. The exact temperature at which the benzotriazole is added will generally depend on the nature of the benzotriazole, particularly its melting point. Higher melting benzotriazoles preferably are added at the higher end of the temperature range, the optimum temperature being capable of determination empirically by means of relatively simple experimentation.

In the conduct of the above-described process, it is desirable to mix the base, benzotriazole, and water in a fashion whereby loss of water by evaporation during the preparation of the complex is minimized. In particular, it is desirable to mix the materials in a closed vessel or, preferably, in a vessel equipped with a condenser such that the water is retained in the vessel even at elevated temperatures. Such practice is generally desirable from the standpoint of reproducibility of melting range, particularly in the case of smaller scale preparations.

The proportions of benzotriazole-base-water which will yield a complex having a melting range above 35° C. have been found to be dependent on the nature of the benzotriazole and the base. Accordingly, for a given benzotriazole and base the water:benzotriazole:base ratios which can be used are determined empirically. Empirical determination of suitable ratios is readily accomplished by simply mixing the components in various ratios under the aforementioned conditions of time and temperature, cooling any resultant single phase liquid to determine if a solid is formed, and thereafter determining the melting range of the solid by procedures well known in the art.

It has been found that, given a particular benzotriazole and base, the base:benzotriazole and water:benzotriazole ratios which can be employed are interdependent, i.e., the water:benzotriazole ratio is determinative of the base:benzotriazole ratios which can be used to produce a complex of this invention and the base:benzotriazole ratio is determinative of the water:benzotriazole ratios which can be used to produce such complexes. In general, base:benzotriazole ratios of about 0.1:1 to about 2:1 and water:benzotriazole ratios of about 5:1 to about 25:1 have been found useful in preparing the complexes of this invention. All ratios reported herein, unless otherwise specified, are molar ratios.

For a given benzotriazole, the particular ratios of water:benzotriazole:base which may be employed to yield a complex have been found to be dependent on the nature of the base, and particularly on the cation provided by the base upon dissociation thereof in water. Thus, the selective employment of different bases providing different cations can serve as a means of modulating the water:benzotriazole and base:benzotriazole ratios which may be employed to produce a complex hereof. A combination of bases which provide different cations may also be employed to effect such modulation including a combination of a base which provides a monovalent metal cation and a base which provides a divalent metal cation.

In addition to being dependent on the nature of the base or combination of bases employed, the particular ratios of water:benzotriazole:base which may be employed to produce a complex of this invention have been found to be dependent on the nature of the benzotriazole. More specifically, it has been found that the substituents $R^1$ and $R^2$ are determinative of appropriate ratios. For example, it has been found that in preparing complexes utilizing sodium hydroxide as the base in the above process, at a given constant base:benzotriazole ratio, higher water:benzotriazole ratios may be employed using 6-methylbenzotriazole rather than benzotriazole per se. Reference may be had to Table I herein demonstrating this effect of a methyl substituent.

Table I summarizes the essential parameters of certain illustrative complexes of this invention prepared as described in Examples 1–12 hereinafter utilizing sodium hydroxide as the base and, as the benzotriazole component, either benzotriazole per se ($R^1$ and $R^2$ are hydrogen) or 6-methylbenzotriazole ($R^1$ is hydrogen, $R^2$ is 6-methyl). A molar sodium hydroxide:benzotriazole ratio of 0.59:1 was used in preparing each of the complexes. The $R^1$ and $R^2$ substituents and molar water:benzotriazole ratio were as indicated in the Table:

TABLE I

| Complex | $R^1$ | $R^2$ | Molar Ratio of Water:Benzo-triazole | Melting Range (°C.) |
|---|---|---|---|---|
| 1 | H | H | 6.6:1 | 58.5–69 |
| 2 | H | H | 7.4:1 | 52–65.5 |
| 3 | H | H | 8.3:1 | 50–63 |
| 4 | H | H | 9.1:1 | 50–64.5 |
| 5 | H | H | 9.9:1 | 37–59 |
| 6 | H | H | 11.6:1 | slurry at 25° C. |
| 7 | H | H | 13.2:1 | slurry at 25° C. |
| 8 | H | CH$_3$ | 8.3:1 | 70–75 |
| 9 | H | CH$_3$ | 9.1:1 | 68–72 |
| 10 | H | CH$_3$ | 9.9:1 | 66–69 |
| 11 | H | CH$_3$ | 11.6:1 | 65–67 |
| 12 | H | CH$_3$ | 13.2:1 | 63–65 |
| 13 | H | CH$_3$ | 14.9:1 | 62–64 |
| 14 | H | CH$_3$ | 16.5:1 | 60–63 |

In addition to demonstrating the previously mentioned effect of a methyl substituent on the water:benzotriazole ratio capable of employment in producing a complex (e.g. compare complexes 11 and 12 with the attempted preparation of complexes 6 and 7), at a constant base:benzotriazole ratio, Table I also demonstrates that substitution of a methyl group for a hydrogen at the 6-position functions to raise the melting range of a complex having a given water:benzotriazole:base ratio (e.g. compare complexes 3–7 with complexes 8–12 respectively).

As further illustration of the effect of substituents $R^1$ and $R^2$, it may be noted that, generally, utilization of 5,6-dimethylbenzotriazole as the benzotriazole component of the complex, tends to result in complexes having higher melting ranges than those observed for corresponding complexes wherein the benzotriazole component is 6-methylbenzotriazole. In addition, higher base:5,6-dimethylbenzotriazole ratios are generally necessary to achieve formation of a single phase liquid. Certain complexes prepared using 5,6-dimethylbenzotriazole and sodium hydroxide are presented in Table II. A molar sodium hydroxide:5,6-dimethylbenzotriazole ratio of 1:1 was employed in preparing the complexes as described in Examples 13–15 hereinafter. The molar water:5,6-dimethylbenzotriazole ratios shown in Table II include as part of the water component amount the water supplied to the complex by employment of 5,6-dimethylbenzotriazole monohydrate:

TABLE II

| Complex | $R^1$ | $R^2$ | Molar Ratio Of Water: 5,6-Dimethylbenzotriazole | Melting Range(°C.) |
|---|---|---|---|---|
| 15 | $CH_3$ | $CH_3$ | 17.8:1 | 52–76 |
| 16 | $CH_3$ | $CH_3$ | 19.5:1 | 44–75 |
| 17 | $CH_3$ | $CH_3$ | 21.2:1 | 43–75 |
| 18 | $CH_3$ | $CH_3$ | 22.8:1 | 42–73 |

The melting range of a complex of this invention may be altered by any of a variety of methods such as by appropriate substitution on the benzotriazole, as exemplified in the data presented in Table I. The melting range may also be altered by employment of different bases in preparing the complex and by modulation of the respective base:benzotriazole and water:benzotriazole ratios. For example, the data in Tables I and II illustrates a lowering of the melting range by increasing the water:benzotriazole ratio while maintaining the base:benzotriazole ratio constant.

The ability to alter the melting range of the complexes of this invention and the ability to produce complexes having different ratios of water:benzotriazole and base:benzotriazole is advantageous in the respect that the complexes of this invention may be prepared having predetermined properties particularly appropriate for employment in thermally processed film units. In particular, complexes having a predetermined and relatively low melting range and capable of providing a relatively large amount of water per weight of complex may be prepared. In addition, complexes may be prepared having a base:benzotriazole ratio sufficient to provide a complex with a high internal pH, e.g., greater than 12, such that the melting of the complex creates a high pH environment within the film unit. It will be appreciated that such an environment may be particularly advantageous for purposes of development of silver halide within the film unit.

Preferred compositions of this invention, particularly for purposes of employment as water-releasing compositions in thermally processed film units, are those having a melting range between about 55° C. to about 90° C.

Bases suitable for use in preparing the complexes of this invention are those capable of dissociating in water to provide an anion and a monovalent or divalent metal cation. Preferred bases are the water-soluble alkali metal hydroxides such as sodium hydroxide and potassium hydroxide and the water-soluble alkaline earth metal hydroxides such as calcium hydroxide. Materials which react in the presence of water to form alkali metal or alkaline earth metal hydroxides, such as sodium, potassium, sodium amide, and calcium oxide, may also be employed in the above process.

The chemical composition and structure of the complexes of this invention are not completely understood. Accordingly, the complexes of this invention are referred to herein as complexes of the materials which interact to produce them, it being understood that the interaction of these materials may produce reaction products which comprise an integral component of the resultant complex. However, the precise nature of any such reaction products, the extent to which they may be formed, and, particularly, the means by which they are associatively related with other components of the complex are not precisely understood. Similarly, the nature of the associative relationship existing between the water and the other components of the complex is not precisely understood although it may be said that a substantial portion of the water appears to be loosely bound or entrapped within the solid structure of the complex.

It is known that benzotriazoles can act as acids in that the proton bonded to the nitrogen atom of the benzotriazole can be given up to a strong base. Thus, while not wishing to be bound to any particular theory, it is believed that the bases used in the above process react to at least a minimal extent with the benzotriazoles to form water-soluble benzotriazole salts of benzotriazole anion and monovalent or divalent metal cation. This type of reaction is illustrated in the following reaction sequence wherein benzotriazole is reacted with sodium hydroxide:

Benzotriazoles are generally only slightly soluble in water. Accordingly, formation of the single phase liquid in the aforementioned process is believed to involve some degree of formation of a water-soluble benzotriazole salt. Complete conversion of the benzotriazole to its salt form is not, however, necessarily essential for formation of the single phase liquid. For example, as indicated by the complexes presented in Table I and as detailed in Examples 1 through 12 hereinafter, sodium hydroxide may be mixed with benzotriazole in a molar ratio of only 0.59:1 with resultant formation of the single phase liquid.

Solidification of the single phase liquid to form the complexes of this invention apparently functions to establish an associative relationship between the components of the liquid such that a substantial portion of the water is bound or entrapped within the structure of the resultant solid in a loose fashion. Melting the solid functions to change the nature or associative relationships of the components of the complex such as to effect a rapid release of the bound or entrapped water in substantial quantity.

In the preparative procedure described above, the postulated salt formation is an in-situ reaction and any benzotriazole salt product is not isolated prior to formation of the solid complex. It will be appreciated that many benzotriazole salts can be isolated. Accordingly, certain of the complexes of this invention may be prepared by adding a previously prepared and isolated benzotriazole salt to water in an amount and at a temperature sufficient to provide a single phase liquid similar to that obtained by in-situ generation of the salt in the above process. The water to which the salt is added may contain any benzotriazole or base necessary to produce the desired complex or such additional materials may be added subsequent to the salt addition.

The complexes of this invention may comprise various addenda other than the water, base, benzotriazole and any reaction products thereof. More specifically, various addenda may be added to either the single phase liquid formed in accordance with procedures described herein, or to a melt of a complex hereof, or to the water used in preparing the complex prior to addition thereto of the base and/or the benzotriazole. Upon solidification of the single phase liquid or the melt comprising such addenda, the addenda are incorporated into the solid structure of the complex. As with the other components of the complex, the associative relationship of the various addenda with the other components of the complex is not precisely understood, although it is believed that the addenda are entrapped within the solid structure of the resultant complex.

It will be appreciated that the addenda should not deleteriously affect any of the properties of the complex, e.g., the melting range or the ability of the complex to release water when melted. Useful addenda for purposes of disposition of the complexes as layers include surfactants and thickeners. Photographic reagents may also be added, e.g., developing agents, stabilizers, toners, and the like. The melting of the complex within a film unit will generally render the photographic reagents available to perform useful functions therein.

As mentioned previously, the complexes of this invention have been found to be useful as thermally induced water-releasing materials in thermally developable film units. More particularly, it has been found that the instant complexes can be included as distinct layers in thermally developabale film units such that application of heat to the film unit melts the complex, thereby effecting release of a substantial portion of the water bound within its solid structure. The released water is accordingly made available to the internal environment of the film unit and may be employed, for example, to activate silver halide developing agents, image stabilizers, and other photographic reagents, and to otherwise facilitate image formation.

The film units of this invention comprise a support carrying on one surface a photosensitive silver halide emulsion layer, a layer comprising a complex of this invention, hereinafter referred to as a water-releasing layer, a silver halide developing agent which may be disposed in the silver halide layer or in the water-releasing layer or in a separate layer preferably positioned between the silver halide layer and water-releasing layer, and a substantially water-impermeable barrier layer positioned within the film unit so as to retain therein the water released from the complex by heating the film unit and melting the complex sufficiently as to permit thermal processing of the film unit. The barrier layer should be capable of sufficiently retaining the released water within the film unit at least during the processing interval. Subsequent to processing, a substantial portion of the released water may be gradually lost to the surrounding environment of the film unit either by gradual diffusion through the barrier layer or by other means, e.g., evaporation through a minor surface or edge of the film unit. In general, such loss of moisture will not adversely affect the photographic image in the film unit and may even be desirable from the standpoint of image stability.

With regard to the functionality of the barrier layer, it should be noted that since a significant portion of the water in a complex of this invention is loosely bound or entrapped within the solid structure of the complex, there can be a tendency for some of this water to be gradually lost to the surrounding environment before use, e.g., by means of evaporation or diffusion out of the complex into an adjacent medium. Accordingly, the barrier layer may provide an additional function in preventing or retarding such loss of water, thereby prolonging the time allowable between the fabrication of the film unit and the exposure and processing thereof.

Figure 1:
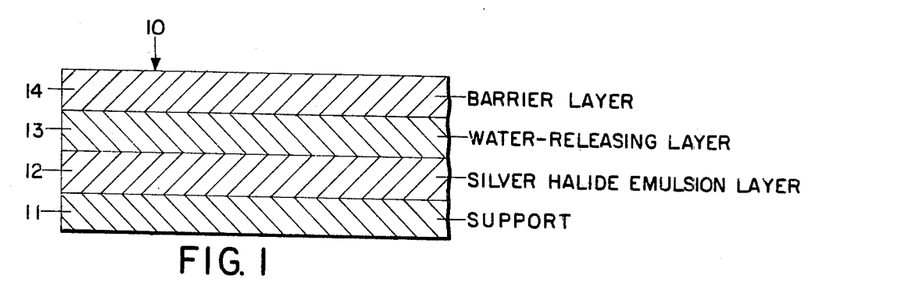
FIG. 1 is a diagrammatic enlarged cross-sectional view of a photographic film unit of this invention.

Referring to FIG. 1, there is shown a diagrammatic enlarged cross-sectional view of a film unit constructed in accordance with the present invention. The film unit 10 is shown to comprise a support member 11, carrying on one surface, in order, a photosensitive silver halide emulsion layer 12, a water-releasing layer 13, and a substantially water-impermeable barrier layer 14. The silver halide developing agent employed within the film unit may be disposed in silver halide layer 12, water-releasing layer 13, or in a separate layer (not shown) preferably positioned between layers 12 and 13.

Figure 2:
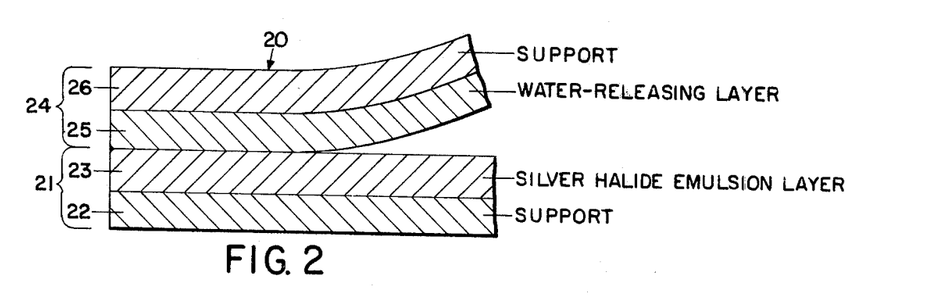
FIG. 2 illustrates one method of preparation of a photographic film unit of the type illustrated in FIG. 1.

Film unit 10 may be fabricated by sequential coating of each of the layers shown on support 11. Alternatively, a film unit of this invention may be fabricated by superposition of two elements as illustratively detailed in FIG. 2. FIG. 2 illustrates a negative element 21, comprising a support member 22 and silver halide emulsion layer 23, and a second sheet-like element 24, hereinafter referred to as processing sheet 24, comprising a second support 26 carrying a water-releasing layer 25. As further illustrated by FIG. 2, a film unit 20 of this invention may be prepared by superposition of elements 21 and 24 with their respective supports outermost. The elements can be brought into superposition prior to exposure of the silver halide provided that at least one of the supports is transparent such that the silver halide may be exposed therethrough. Preferably, the elements are superposed subsequent to exposure such that the amount of time during which silver halide layer 23 and water-releasing layer 25 are in contact prior to processing is minimized. It will be understood that support 26 should be substantially water-impermeable in the same fashion as barrier layer 14 such that, subsequent to superposition, it provides the same functionality to the film unit as barrier layer 14 and may be considered equivalent thereto. The silver halide developing agent of the film unit may be contained in either negative element 21 or processing sheet 24. Processing sheet 24 may also comprise, prior to superposition with negative element 21, a removable protective overcoat layer. This protective layer should be substantially water-impermeable so as to prevent the inadvertent loss of any of the loosely bound water from the water-releasing composition prior to superposition with negative element 21. Materials which are particularly suitable as such protective layers are substantially water-impermeable polymeric sheet materials, e.g., sheets of polyethylene, polyvinylidene chloride, polytetrafluoroethylene, polyvinylchloride, polyvinylacetate, and polyethyleneglycol terephthalate. The protective layer is stripped or peeled away from the processing sheet prior to superposition with the negative element.

The film units of this invention may also be fabricated by bringing a barrier layer, e.g., barrier layer 14 of FIG.

1, into superposition with the external surface of the outermost layer of a negative element, e.g., the external surface of silver halide layer 23 of negative element 21 in FIG. 2, and disposing the water-releasing layer therebetween. In accordance with this method of fabrication the water-releasing layer may be disposed between the barrier layer and the outermost layer of the negative element concurrent with or subsequent to superposition thereof. It is preferred that the barrier layer employed for such a method of fabrication be a substantially water-impermeable flexible sheet material.

For purposes of fabricating layers of the water-releasing compositions of this invention, the solid water-releasing complexes may be melted and the melt coated or otherwise disposed so as to form a layer. The melt may then be cooled to effect solidification thereof, thereby re-forming the water-releasing composition as a discrete layer.

Rather than fabricating the water-releasing layer from a melt of the water-releasing composition, the single phase liquid obtained by the procedures described herein may be employed. Accordingly, the single phase liquid may be coated or otherwise disposed to form a layer and thereafter cooled to effect initial formation of the water-releasing complex as a discrete layer.

The method of disposing a melt of the water-releasing complex between superposed elements may also be used in fabrication of the aforementioned processing sheet 24, e.g., the aforementioned removable protective layer may be superposed with support 26 and the melt of the complex disposed therebetween.

Figure 3:
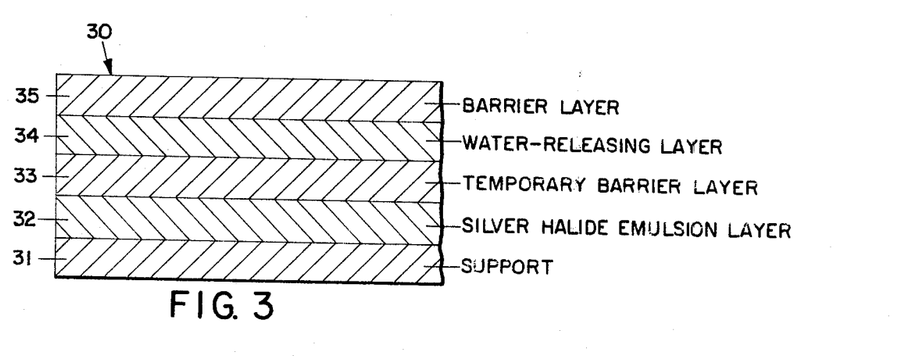
FIG. 3 is a diagrammatic enlarged cross-sectional view of another photographic film unit of this invention.

In FIG. 3 of the accompanying drawings there is shown a film unit 30 comprising a support member 31, carrying on one surface, in order, a silver halide emulsion layer 32, a temporary barrier layer 33, a water-releasing layer 34, and a barrier layer 35. The properties of the temporary barrier layer 33 are such that it is substantially water- and alkali-impermeable at temperatures of storage of the film unit but substantially water- and alkali-permeable at the processing temperature. Layer 33 thus allows the water and alkali contained in layer 34 to gain access to silver halide layer 32 and other layers similarly positioned in the film unit with respect to layer 33 essentially only during processing, thereby preventing inadvertent and premature contact of the silver halide and other similarly positioned layers with the water and alkali. The layer 33 may be coated in sequence with the other layers of the film unit or it may be coated on a processing sheet such as processing sheet 24 of FIG. 2, preferably as an overcoat, and become a part of the laminar assembly of the film unit upon superposition of the processing sheet on a negative element. When coated on the processing sheet, the temporary barrier layer may function to prevent the inadvertent loss of any of the loosely bound water of the water-releasing composition in a fashion similar to the removable protective layer mentioned previously.

Materials which may be employed in temporary barrier layer 33 are those which are capable of undergoing a physical or chemical change at or slightly below the processing temperature to convert the layer from a substantially water- and alkali-impermeable to a substantially water- and alkali-permeable condition. Materials which may be used include low melting polymers and the various animal, mineral, and vegetable waxes such as beeswax, paraffin wax cotton wax, carnauba wax, and the like.

The supports employed in the film units of this invention may be opaque or transparent as appropriate for a given photographic process. The supports may comprise any of the rigid or flexible sheet materials, for example, glass, paper, and polymeric films of both the natural and synthetic types. Especially suitable sheet materials comprise flexible synthetic polymers such as polymethacrylic acid, methyl and ethyl esters; vinyl chloride polymers; vinylidene chloride polymers; polyvinyl acetals; polyamides such as nylon; polyesters such as the polymeric films derived from ethylene glycol terephthalic acid; polymeric cellulose derivatives such as cellulose acetate, triacetate, nitrate, propionate, butyrate, acetatebutyrate, or acetate propionate; polycarbonates; and the like.

Silver halides which may be employed as the photosensitive component of the film units of this invention include silver chloride, silver bromide, and silver iodide and mixed silver halides such as silver chlorobromide, silver chloroiodobromide, and silver iodobromide. Preferably, the silver halide is dispersed in a water-permeable and swellable binder material such as an appropriate synthetic polymer material or, preferably, a gelatin matrix. The silver halide may be monochromatically or panchromatically sensitized by optical sensitizing dyes in accordance with procedures known in the art.

Silver halide developing agents which may be employed in the film units of the present invention include hydroquinone and derivatives of hydroquinone such as 4'-methylphenylhydroquinone, catechol and derivatives of catechol such as 4-phenylcatechol, aminophenols such as N-methyl-p-aminophenol, the 3-pyrazolidones such as 1-phenyl-3-pyrazolidone, and reductones such as 2-hydroxy-3-amino-4,4,6,6-tetramethyl-2,3-cyclohexeneone.

Barrier layers employed in the film units of this invention comprise a material capable of rendering the layer substantially impermeable to water over the range of temperatures employed in the fabrication, storage, and processing of the film unit. The barrier layer may be a coating of such a material, e.g., a coating of a polymer, or it may be a preformed sheet of such material which is superposed with the remaining layers of the film unit. Especially suitable sheet materials are polymeric materials which can be coated, cast or otherwise disposed to form substantially water-impermeable layers or sheets. Any of the rigid or flexible polymeric sheet materials denoted above as suitable for use as supports in the film units of this invention can also be employed therein as barrier layers. Paper sheets coated with a suitable water-impermeable polymer may also be employed. Subsequent to processing, the barrier layer may be stripped from the film unit or it may be retained as an integral layer thereof.

The film units of this invention may comprise layers in addition to those specifically illustrated in FIGS. 1–3, e.g., a layer comprising an image stabilizer such as sodium thiosulfate, a gelatin layer positioned, for example, on that side of the silver halide emulsion layer opposite the film unit support and designed to minimize pressure fogging of the silver halide emulsion, or a reflective layer against which the image produced in the film unit may be viewed.

Image formation in the film units of this invention may be accomplished by exposing the film unit; heating the film unit to a temperature sufficient to melt the water-releasing composition; and maintaining the film unit at a processing temperature for a period of time effective to provide an image to the film unit. Generally, the processing temperature is the temperature to which the film unit is heated to melt the water-releasing composition. Thus, in a typical process, the film unit is heated to a given temperature to effect melting of the water-releasing composition and thereafter maintained at that temperature for a period of time effective to provide an image to the film unit. It will be understood, however, that the processing temperature may be above or below the temperature to which the film unit is heated to effect melting of the water-releasing composition.

Exposure of the silver halide may be made through the support layer or barrier layer of the film unit or, as mentioned previously, a negative element, such as negative element 21 of FIG. 2, may be exposed prior to superposition with a processing sheet comprising a layer of a water-releasing composition of this invention.

The film unit may be heated, for example, by contacting either or both of the external principal surfaces of the unit with a heated platen, by placing the film unit in an oven, or by other suitable means.

Inasmuch as the water-releasing compositions may be formulated so as to release water in a variety of predetermined temperature ranges, they provide flexibility in the choice of the temperature or temperatures used to effect processing. In particular, relatively low temperatures, e.g., less than 100° C. may be employed consistent with the objective of optimizing the quality of the photographic image. Thus, for example, employment of relatively low temperatures tends to minimize heat fogging of the silver halide emulsion, thereby facilitating formation of images of satisfactory contrast. Generally, temperatures in the range of about 55° C. to about 90° C. are preferred, the exact temperature being dependent on the particular melting range of the water-releasing composition and on the development and image formation characteristics of the film unit components. The film unit is maintained at the processing temperature at least for a period of time effective to provide an image to the film unit. Generally, film units fabricated in accordance with the disclosures herein may be heated for a period of one to thirty minutes to effect image formation.

Image formation within the film unit occurs as a result of development of the silver halide by the silver halide developer. For example, in film units designed to provide silver images, the latent image resultant from photoexposure of the silver halide can be developed to a silver image during processing of the film unit. Both negative and positive images may be produced depending on the type of silver halide emulsion employed. Thus, negative silver images may be produced employing conventional negative-working emulsions wherein a developable latent image is formed in terms of areas of photoexposure. Positive silver images may be produced employing direct positive emulsions, i.e., emulsions wherein the developable latent image existent subsequent to exposure is in unexposed areas.

Relatively stable silver images may be obtained in the film units of this invention wherein the latent image is developed to a silver image without post-processing treatment with stabilizers, fixers, and the like, and without including special stabilizing agents in the film unit. Apparently, the benzotriazole of the water-releasing composition is capable of forming a relatively light-insensitive complex with the silver halide not reduced to image silver during processing, thereby minimizing discoloration or darkening of the image in the $D_{min}$ areas upon exposure of the image to light. This stabilization of the image resultant from the employment of the water-releasing compositions hereof accordingly obviates the inclusion of additional image stabilizers in the film unit although such materials may be included if desired.

The images produced in the film units of this invention may be viewed as transparencies if the support layer and the barrier layer, if maintained in integral contact with the film unit subsequent to processing, are transparent. The images may alternatively provide reflection prints if a suitable reflective background is provided, e.g., a reflective background provided by a support or by a layer of a reflective material such as titanium dioxide.

The complexes of this invention are intended for use in any type of thermally developable film unit in which a thermally induced water-releasing material is desired. Accordingly, use of the complexes is not limited to the photographic film units and processes described with particularly herein. The complexes may be employed, for example, in thermally developable film units adapted to provide color images or positive silver diffusion transfer images.

The present invention is further illustrated in the following Examples which are illustrative only and not intended to be of limiting effect.

EXAMPLE 1

Preparation of Complex 1 in Table I:

0.8 grams of sodium hydroxide were dissolved in 4.0 ml. of water at an ambient temperature of about 25° C. The solution was heated to about 55° C. and 4.0 g. of benzotriazole were then added with stirring. A clear, one-phase liquid was obtained almost immediately and was cooled to about 25° C. to produce a waxy solid having a melting range of about 50.5°–64.5° C.

EXAMPLES 2–5

Complexes 2 through 5 in Table I were prepared in the manner described in Example 1 except that the amounts of water were, respectively, 4.5 ml., 5.0 ml., 5.5 ml., and 6.0 ml., thereby progressively increasing the molar water:benzotriazole ratio as indicated in Table I. The melting ranges of the resultant waxy solids were as indicated in Table I.

Solid complexes were not obtained by carrying out the procedure of Example 1 using 7.0 ml. and 8.0 ml. of water (molar water:benzotriazole ratios of 11.6:1 and 13.2:1, respectively), the resultant mixtures being slurries at room temperature of about 25° C. as indicated in Table 1.

EXAMPLE 6

Preparation of Complex 8 in Table I:

0.8 grams of sodium hydroxide, 4.47 g. of 6-methylbenzotriazole, and 5 ml. of water were mixed in a three-necked round bottom flask equipped with a thermometer, stirrer and reflux condenser. The materials were mixed at ambient room temperature of about 25° C. The mixture was heated on a steam bath to a temperature between about 60° C. to about 70° C. for a period of time sufficient to form a single phase liquid (about 1 to 5 minutes). The single phase liquid was cooled to about 25° C. to produce a waxy solid having a melting range of about 70°–75° C.

EXAMPLES 7-12

Complexes 9 through 14 in Table I were prepared in the manner described in Example 6 except that the amounts of water were, respectively, 5.5 ml., 6.0 ml., 7.0 ml., 8.0 ml., 9.0 ml., and 10.0 ml., thereby progressively increasing the molar water:6-methylbenzotriazole ratio as indicated in Table I. The melting ranges of the resultant waxy solids were as indicated in Table I.

EXAMPLE 13

Preparation of Complex 15 in Table II:

0.134 grams of sodium hydroxide were dissolved in 1.0 ml. of water in a three-necked round bottom flask equipped with a thermometer, stirrer, and reflux condenser. The solution was heated to about 90° C. and 0.545 g. of 5,6-dimethyl(1H)benzotriazole monohydrate were then added. The molar water:5,6-dimethyl(1H-)benzotriazole:sodium hydroxide ratio, as indicated by Table II, was accordingly 17.8:1:1 wherein the water component was calculated to include the water supplied to the complex by employment of the monohydrate of 5,6-dimethyl(1H)benzotriazole. The mixture was maintained at about 90° C. until a clear one phase liquid was obtained which was cooled to about 25° C. to produce a tan solid having a melting range of about 52°-76° C.

EXAMPLES 14-16

Complexes 16-18 in Table II were prepared in the manner described in Example 13 except that the amounts of water were, respectively, 1.1 ml., 1.2 ml., and 1.3 ml., thereby progressively increasing the molar water:5,6-dimethyl(1H)benzotriazole ratios as indicated in Table II. The melting ranges of the resultant solids were as indicated in Table II.

EXAMPLE 17

A complex of this invention comprising a combination of bases was prepared as follows:

20 ml. of water and 20 ml. of a 5% aqueous solution of polyethylene oxide thickener (available from Union Carbide Corp. under the tradename Polyox) were mixed at room temperature and heated to about 75° C. Three grams of benzotriazole were then added with stirring. A solution of 3 g. of sodium hydroxide in 20 ml. of water was then added slowly and the stirring continued until a single phase liquid had been formed. Thereafter 9.425 g. of calcium oxide were added slowly. The resultant salmon colored viscous liquid solidified on cooling to 25° C. into a white waxy solid having a melting range of about 63°-65° C.

EXAMPLE 18

A photosensitive element was prepared by coating, in succession, on a transparent polyethylene glycol terephthalate base:

1. a layer of a conventional negative-working gelatino silver iodobromide emulsion at a coverage of about 1180 mg./m² of silver and about 950 mg./m² of gelatin;
2. a layer of gelatin at a coverage of about 320 mg./m².; and
3. a layer of a 10% by weight dispersion of 2-hydroxy-3-amino-4,4,6,6,-tetramethyl-2,3-cyclohexeneone in poly-N-vinylpyrrolidone at a coverage of about 1000 mg./m². of the cyclohexeneone.

A transparent sheet of polyethylene glycol terephthalate was brought into superposition with the external surface of the cyclohexeneone-poly-N-vinylpyrrolidone layer and a rupturable container retaining a melt of the complex prepared in Example 13 was fixedly mounted transverse the leading edge of the respective superposed sheet and negative element. Before the melt of the complex had cooled sufficiently to solidify, the resultant unit was passed into and through a pair of pressure rollers positioned at a distance of 0.0006 inch from one another thereby rupturing the rupturable container and effecting disposition of the melt as a layer positioned between the inner surface of the superposed polyethylene glycol terephthalate sheet and the cyclohexeneone-poly-N-vinylpyrrolidone layer. The layer of the melt was allowed to cool, thereupon solidifying to a solid layer. The resultant film unit was given a 4 meter-candle-second exposure through a graduated neutral density wedge target and placed in a 76° C. oven for 10 minutes to effect thermal processing thereof. A negative silver image was obtained which was viewed as a transparency without removal of the sheet of polyethylene glycol terephthalate.

It will be understood that the water-releasing composition prepared in Example 13 and used in the film unit of this Example comprised an amount of sodium hydroxide sufficient to provide to the film unit an internal environment of pH 12 or greater during processing.

Since certain changes may be made in the above products and processes without departing from the scope of the invention herein involved, it is intended that all matter contained in the above description shall be interpreted as illustrative and not in a limiting sense.

What is claimed is:

1. A solid composition having a releasable content of water and comprising a complex of water, a benzotriazole of the formula wherein $R^1$ and $R^2$ are independently hydrogen, a monovalent organic radical, halogen, or nitro, and at least one water-soluble base having a basicity greater than that of said benzotriazole and capable of dissociating to provide an anion and a mono-valent or divalent metal cation, said water, benzotriazole and water-soluble base being in proportions such that the complex has a melting range above 35° C., said complex being capable of releasing a substantial portion of said water content by the melting thereof.

2. A composition of claim 1 wherein said monovalent organic radical is selected from the group consisting of lower alkyl, aryl, alkaryl, aralkyl, and lower alkoxy.

3. A composition of claim 1 wherein $R^1$ and $R^2$ are hydrogen.

4. A composition of claim 1 wherein at least one of $R^1$ and $R^2$ is other than hydrogen.

5. A composition of claim 1 wherein said benzotriazole is of the formula wherein $R^1$ and $R^2$ are independently hydrogen, a monovalent organic radical, halogen, or nitro.

6. A composition of claim 5 wherein one of $R^1$ and $R^2$ is hydrogen and the other is lower alkyl.

7. A composition of claim 6 wherein one of $R^1$ and $R^2$ is hydrogen and the other is methyl.

8. A composition of claim 5 wherein $R^1$ and $R^2$ are methyl.

9. A composition of claim 1 wherein said monovalent metal cation is an alkali metal cation.

10. A composition of claim 1 wherein said divalent metal cation is an alkaline earth metal cation.

11. A composition of claim 1 wherein said base is selected from the group consisting of alkali metal hydroxides and alkaline earth metal hydroxides.

12. A composition of claim 11 wherein said base is selected from the group consisting of potassium hydroxide, sodium hydroxide, and calcium hydroxide.

13. A composition of claim 1 wherein said melting range is between about 55° C. and about 90° C.

14. A process for preparing a solid complex having a releasable content of water, said process comprising the steps of mixing water, a benzotriazole of the formula wherein $R^1$ and $R^2$ are independently hydrogen, a monovalent organic radical, halogen, or nitro, and at least one water-soluble base having a basicity greater than that of said benzotriazole and capable of dissociating to provide an anion and a monovalent or divalent metal cation, said mixing being conducted under conditions of time and temperature such that a single phase liquid is obtained; and cooling said single phase liquid to a temperature at which it is converted to a solid complex; said benzotriazole, base, and water being mixed in proportions such that said solid complex possesses a melting range above 35° C. and is capable of releasing a substantial portion of said water content by the melting thereof.

15. A process of claim 14 wherein said benzotriazole, base, and water are mixed at about 25° C. and heated to effect formation of said single phase liquid.

16. A process of claim 14 wherein said benzotriazole, base, and water are mixed at a temperature of about 40° C. to 100° C.

17. A process of claim 16 wherein said benzotriazole, base, and water are mixed at a temperature of about 55° C. to 90° C.

18. A process of claim 14 wherein said base and said benzotriazole are mixed in a molar ratio of about 0.1:1 to about 2:1 base:benzotriazole and said water and said benzotriazole are mixed in a molar ratio of about 5:1 to about 25:1 water:benzotriazole.

19. A process of claim 14 wherein said monovalent organic radical is selected from the group consisting of lower alkyl, aryl, alkaryl, aralkyl, and lower alkoxy.

20. A process of claim 14 wherein $R^1$ and $R^2$ are hydrogen.

21. A process of claim 14 wherein at least one of $R^1$ and $R^2$ is other than hydrogen.

22. A process of claim 14 wherein said benzotriazole is of the formula wherein $R^1$ and $R^2$ are independently hydrogen, a monovalent organic radical, halogen, or nitro.

23. A process of claim 22 wherein one of $R^1$ and $R^2$ is hydrogen and the other is lower alkyl.

24. A process of claim 23 wherein one of $R^1$ and $R^2$ is hydrogen and the other is methyl.

25. A process of claim 22 wherein $R^1$ and $R^2$ are methyl.

26. A process of claim 14 wherein said monovalent metal cation is an alkali metal cation.

27. A process of claim 14 wherein said divalent metal cation is an alkaline earth metal cation.

28. A process of claim 14 wherein said base is selected from the group consisting of alkali metal hydroxides and alkaline earth metal hydroxides.

29. A process of claim 28 wherein said base is selected from the group consisting of potassium hydroxide, sodium hydroxide, and calcium hydroxide.

30. A process of claim 14 wherein two or more of said water-soluble bases are used in combination.

31. A process of claim 14 wherein said melting range of said solid is between 55° C. and 90° C.

32. A solid composition prepared in accordance with the process of claim 14.

* * * * *